United States Patent

Szpara et al.

[11] Patent Number: 5,924,452
[45] Date of Patent: Jul. 20, 1999

[54] VALVE ASSEMBLY

[75] Inventors: Edward Szpara, St. Charles; Sarah L. Corbin, Hawthorn Woods; James C. Richardson, Schaumburg; Lewis E. Daniels, Jr., Wonder Lake, all of Ill.

[73] Assignee: Baxter International Inc., Deerfield, Ill.

[21] Appl. No.: 08/925,219

[22] Filed: Sep. 8, 1997

Related U.S. Application Data

[51] Int. Cl.$^6$ ................................................. F16K 15/14
[52] U.S. Cl. .......................... 137/846; 137/844; 137/847
[58] Field of Search ................................... 137/846, 844, 137/843, 847

[56] References Cited

U.S. PATENT DOCUMENTS

| | | |
|---|---|---|
| 2,605,784 | 8/1952 | Snider . |
| 3,710,942 | 1/1973 | Rosenberg ............................ 137/846 |
| 4,434,810 | 3/1984 | Atkinson . |
| 4,535,818 | 8/1985 | Duncal et al. . |
| 4,535,819 | 8/1985 | Atkinson et al. . |
| 4,566,493 | 1/1986 | Edwards et al. . |
| 4,612,960 | 9/1986 | Edwards et al. . |
| 4,809,679 | 3/1989 | Shimonaka et al. . |
| 4,810,123 | 3/1989 | Bruggeman . |
| 4,828,554 | 5/1989 | Griffin ..................................... 137/846 |
| 4,948,092 | 8/1990 | Kasper et al. . |
| 5,010,925 | 4/1991 | Atkinson et al. . |
| 5,125,903 | 6/1992 | McLaughlin et al. . |
| 5,261,459 | 11/1993 | Atkinson et al. . |
| 5,273,546 | 12/1993 | McLaughlin et al. . |
| 5,398,853 | 3/1995 | Latham . |
| 5,474,099 | 12/1995 | Boehmer et al. . |

*Primary Examiner*—Denise L. Ferensic
*Assistant Examiner*—Joanne Y. Kim
*Attorney, Agent, or Firm*—Jeffrey C. Nichols; Mark J. Buonaiuto; Frances C. Kowalik

[57] ABSTRACT

A valve assembly for permitting fluid flow in a first direction and for preventing fluid flow in a second direction opposite to the first direction. The valve assembly includes an upper housing, a lower housing coupled to the upper housing to form a generally axially extending housing assembly, and a valve seating section defined within an inner peripheral portion of the lower housing. The valve seating section includes an axially extending inner peripheral surface and a transversely extending surface substantially normal to the axially extending inner peripheral surface. A valve member is seated within the valve seating section of said lower housing. The valve member includes a flange that extends from the valve member in a transverse direction and defines an axially oriented outer peripheral surface thereof. The valve member is retained within the valve seating section of the lower housing by the axially extending inner peripheral surface of the valve seating section transversely compressing the axially oriented outer peripheral surface of the flange to form a press-fit therebetween. Further, the valve member also includes a lower transverse surface which is axially separated from the transversely extending surface of the valve seating section, in which an air space is defined between these two transverse surfaces.

29 Claims, 3 Drawing Sheets

FIG. 4
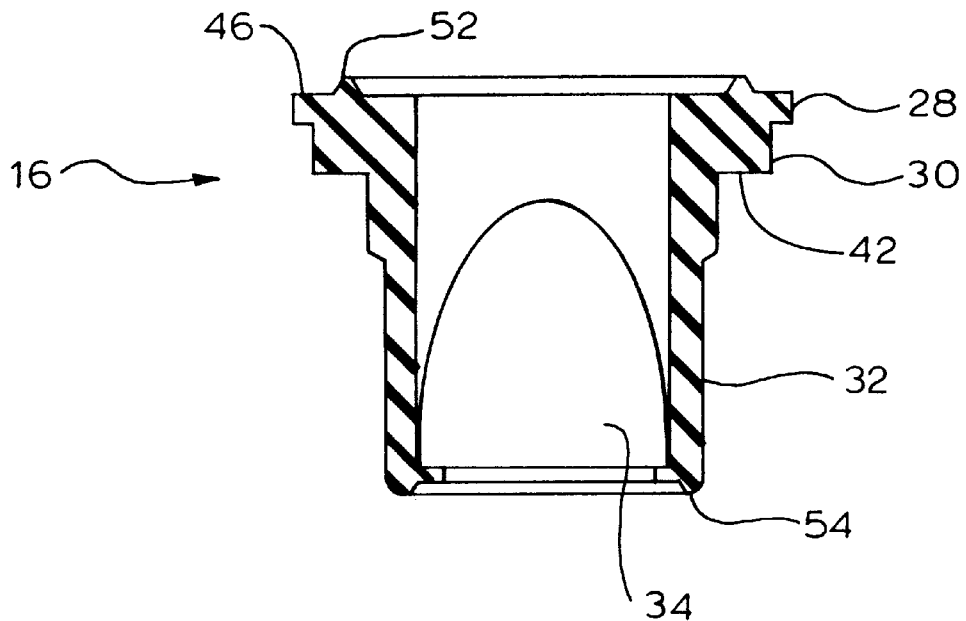
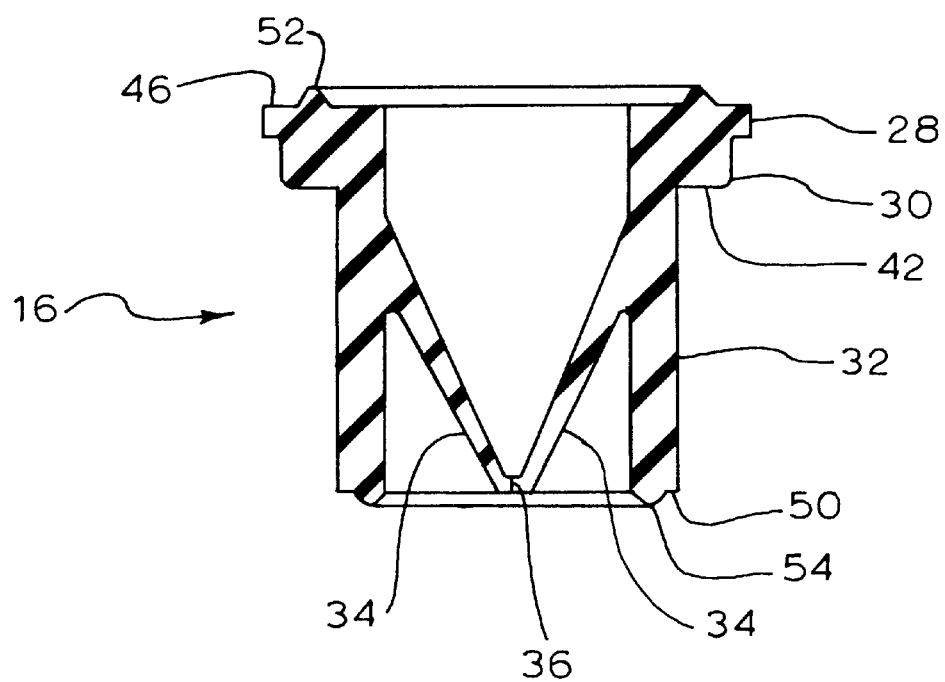
FIG. 5

VALVE ASSEMBLY

BACKGROUND

The present invention relates generally to a valve and valve assembly, and more particularly to a normally closed valve for use in intravenous medical applications, where the valve is retained in a housing primarily by way of radial forces created by a press fit between a flange on the valve and an inner peripheral surface of the housing.

Although other configurations and intended uses are contemplated, the preferred embodiment of the present invention is a duckbill valve for use in administering fluid to a patient through a Y-site arrangement where two different fluid lines are combined at the Y-site, and where the duckbill valve permits one of the fluids from a first fluid line to flow in a first direction to the patient, but prevents the other fluid from flowing up the first line in the opposite direction to contaminate the supply of the first fluid.

Typically, Y-site valve arrangements are utilized to combine fluids from two different fluid lines, where one line typically provides a continuous flow of saline or equivalent fluid, and the other line generally provides a flow of a predetermined quantity of medication. The two fluids are combined at the Y-site, and the fluid blend is then administered to the patient intravenously. The leg of the Y-site that is connected to the saline line generally includes a valve that allows the saline to flow towards the patient, but does not allow the saline, or, more importantly, the medication from the other line, to flow in the opposite direction. Such a valve prevents the medication from contaminating the saline supply, which may result in the improper dosage of medication being delivered to the patient.

In prior art arrangements, the valve is generally contained within a two part housing assembly, consisting of an upper housing part and a lower housing part. The two parts of the housing assembly are generally made of plastic, and are welded together. The valve is typically seated on a shoulder that is defined on the lower part of the housing assembly, and the valve is maintained in position by axial forces created from the upper part when the two parts of the housing assembly are welded together.

Several problems may result from the valve being axially compressed within the upper and lower housing parts. First, if the axial forces on the valve are not relatively uniformly distributed around the upper surface of the valve, the valve may not be seated properly within the housing, i.e., the valve may be somewhat inclined within the housing. An inclined valve has an increased probability of failure by either not opening at the desired cracking pressure, or by not closing at the desired back pressure.

Either of these types of failure may occur in a duckbill valve, which includes a pair of resilient lips, in which the lips converge in a normally closed slit-like aperture. Failure of a duckbill valve may occur where the lips inadvertently come into contact with the inner walls of the housing assembly. Such contact may prevent the resilient lips from properly opening or closing at the desired pressures. Due to the small size of the valve assembly and the low pressures involved, there is only a very small range of pressures within which the valve must operate. Thus, the valves are extremely sensitive, and even small inaccuracies resulting from assembly errors or tolerance errors can possibly result in failure.

In addition to the problems associated with contact between the lips and the housing, it is also somewhat difficult to obtain consistent welds between the housing components due to the inclusion of a third component, the valve, which is sandwiched between the two housing components. Inconsistent welds may occur because the spacing between the two housing components is not always uniform due to the valve being interposed between the two housing parts.

Consequently, in response to the these problems, it is one object of the present invention to provide an improved valve assembly design that is less susceptible to failure and leakage than other designs where the valve is retained between two housing components via axial compression.

Another object is to provide a design for an improved valve assembly where it is possible to obtain consistent and reliable welds between the two housing components because the valve is no longer involved in the welding process.

A further object of the present invention is to provide a design for an improved valve assembly where the valves may be consistently properly seated within the housings, without the valves being inclined with respect to the housings, so that this potential source of valve failure is substantially eliminated.

A related object of the present invention is to supply a design for an improved valve assembly where the valves each include a pair of resilient lips that converge to form a normally closed slit-like aperture and where the valves are each seated within a housing in such a manner that the resilient lips are consistently out of contact with the inner peripheries of the housings.

It is yet another object of the present invention to provide an improved valve assembly where the valve is retained within the housing via radial compression.

Still another object of the invention is to supply an improved valve assembly where the valve includes a shoulder and the valve is seated within the housing via radial compression such that an air space is created between the lower surface of the shoulder of the valve and the housing.

Yet another object of the present invention is to provide an improved valve assembly in which the valve is maintained in the housing without relying upon axial compression.

These and other objects of the present invention will be apparent from the following detailed description of the invention, while referring to the attached drawings, in which:

FIG. 4 is a cross-sectional view of a preferred embodiment of the valve member of the present invention, taken along lines IV—IV shown in FIG. 3.

FIG. 5 is a another cross-sectional view of a preferred embodiment of the valve member of the present invention, taken along lines V—V shown in FIG. 3.

The above-listed objects are met or exceeded by the present apparatus that provides an improved valve assembly. Generally, the valve assembly of the present invention includes three major components—a valve member, an upper housing, and a lower housing. After the valve member is seated within the lower housing, the upper housing and the lower housing are welded together to form a housing assembly. Consistent, reliable seating of the valve member is obtained by configuring the valve member to be radially press-fit within the lower housing, instead of relying upon axial compression from the upper housing part to secure the valve member in place. By utilizing radial compression to seat the valve member, the valve member will be properly centered and aligned, which will avoid the types of failure that could result from an inclined or otherwise improperly seated valve member.

More specifically, the present invention is directed to an improved valve assembly for permitting fluid flow in a first direction and for preventing fluid flow in a second direction opposite to the first direction. The valve assembly includes an upper housing, a lower housing coupled to the upper housing to form a generally axially extending housing assembly, and a valve seating section defined within an inner peripheral portion of the lower housing. The valve seating section includes an axially extending inner peripheral surface and a transversely extending surface substantially normal to the axially extending inner peripheral surface. A valve member is seated within the valve seating section of the lower housing. The valve member includes a flange that extends from the valve member in a transverse direction and defines an axially oriented outer peripheral surface thereof. The valve member is retained within the valve seating section of the lower housing by the axially extending inner peripheral surface of the valve seating section transversely compressing the axially oriented outer peripheral surface of the flange to form a press-fit therebetween. Further, the valve member also includes a lower transverse surface which is axially separated from the transversely extending surface of the valve seating section, in which an air space is defined between these two transverse surfaces.

DETAILED DESCRIPTION OF THE PREFERRED EMBODIMENTS

Figure 1:
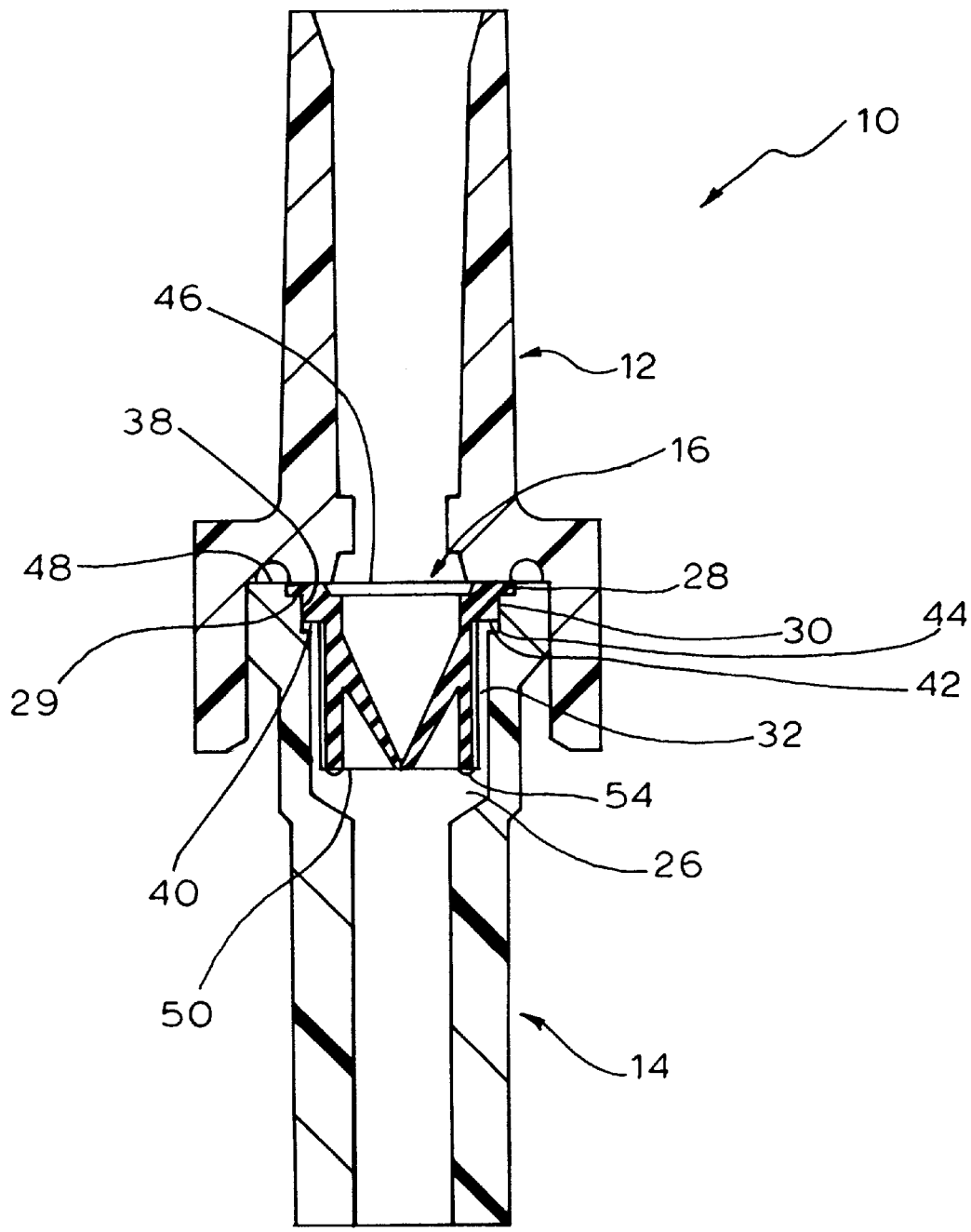
FIG. 1 is a cross-sectional view of a preferred embodiment of the present valve assembly.
Figure 2:
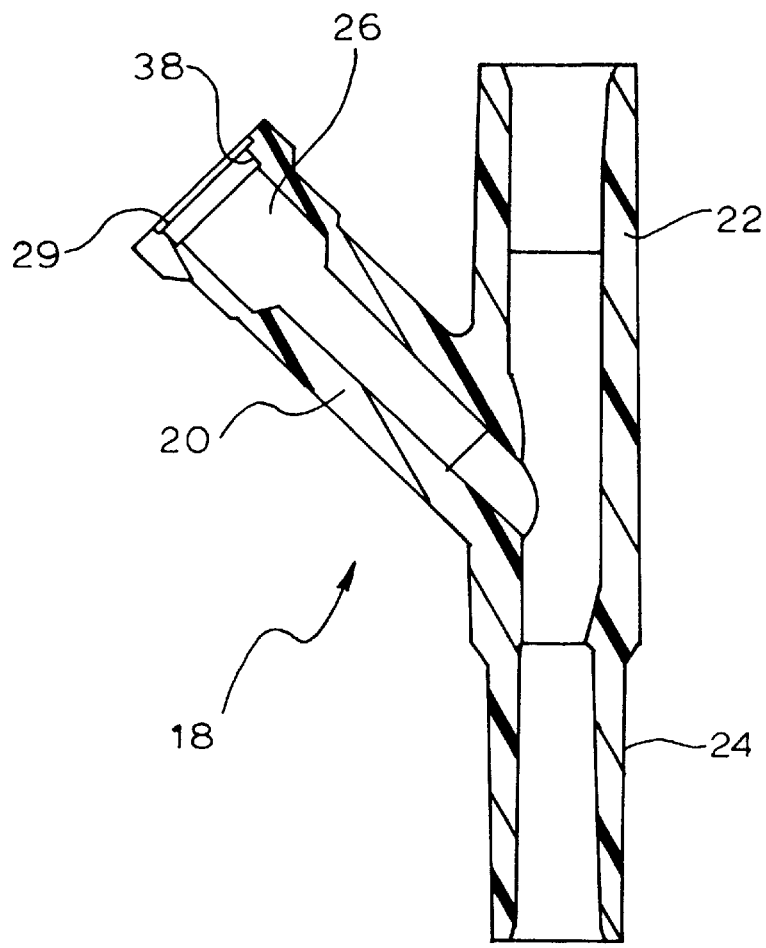
FIG. 2 is a cross-sectional view of a Y-site with a lower part of the housing of the present invention formed integrally therewith.
Figure 3:
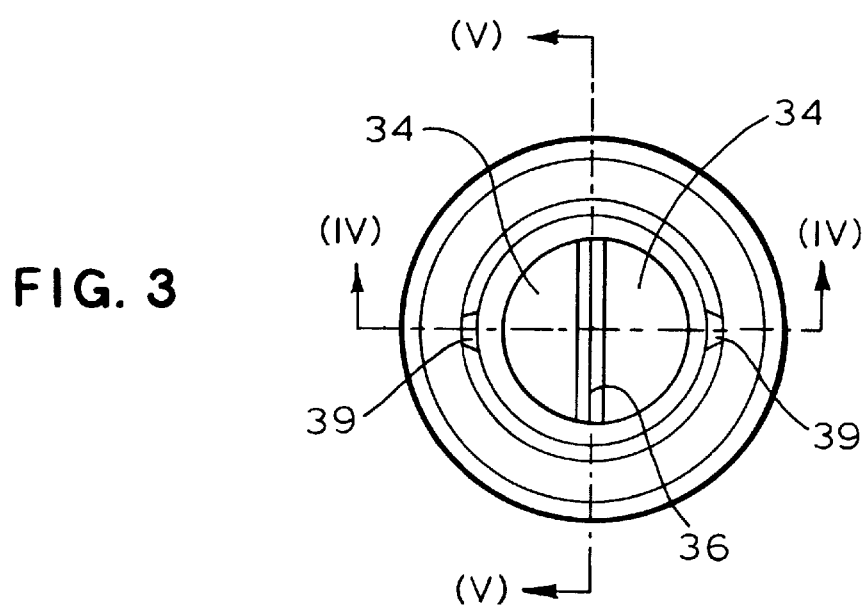
FIG. 3 is a top view of the preferred embodiment of the present valve member.

Referring now to the drawings, the preferred embodiment of the present valve assembly is shown in FIGS. 1–5, with FIG. 1 showing the completely assembled present valve assembly, indicated generally as 10. The valve assembly 10 is composed of an upper housing 12, a lower housing 14 and a valve member 16. The upper housing 12 and the lower housing 14 are preferably made from a substantially rigid material, such as acrylic. The valve member 16 is preferably formed from an elastomeric material such as an elastomeric silicone, or preferably from a synthetic polyisoprene. Optionally, the material of the valve member may also include an oil or other lubricant, which would continuously "bloom" to the surface of the valve and act as a lubricant to prevent the valve from sticking closed. The valve assembly 10 may be incorporated into a Y-site 18, which is shown in FIG. 2. The Y-site 18 includes a first leg 20 for delivering fluid from a first fluid line, and a second leg 22 for delivering fluid from a second fluid line. The two fluids are combined at the lower leg 24, where the fluid blend can then be administered to the patient intravenously.

In the Y-site 18, the first leg 20 serves as the lower housing. The first leg 20 is typically the line which administers the saline solution (or its equivalent), while the second leg 22 is typically the line which administers the medication. The first leg 20 includes a valve seating section 26, which is designed to seat the valve member 16 (shown in FIG. 1). The valve member 16 functions as a one way check valve which permits fluid from the first line (typically saline solution) to pass through the first leg 20 towards the patient, while preventing fluid from the second line (typically the medication), which has passed through the second leg 22, from flowing up the first leg 20. Thus, the valve member 16 prevents fluids in the lower leg 24 from contaminating the supply of saline solution.

Referring now to FIGS. 4 and 5, the valve member 16 is shown as having a collar 28 and a flange 30. The valve member 16 further includes a main body portion or barrel portion 32, which is a generally cylindrical section (see also FIG. 3) that extends below the flange 30. To add strength to the valve member 16, a pair of ribs 39 (see FIGS. 3 and 4) may optionally be formed on the outer periphery of the barrel portion 32. Located within the barrel portion 32 are a pair of lips 34. Each lip 34 is a substantially planar member that extends from the inner periphery of the barrel portion 32 towards the bottom of the valve member 16. The two lips 34 resiliently converge at an aperture 36. The aperture 36 is preferably in the form of a slit, which can be cut into the valve member 16 after it has been molded in a manner known to those of ordinary skill in the art. The resilient lips 34 normally maintain the slit 36 in the closed position. However, a slight increase in pressure in the area above the lips 34 causes the slit 36 to open, permitting fluid to flow downwardly through the valve member 16. The slit 36 can be caused to close if the pressure below the lips 34 is higher than the pressure above the lips by more than a certain minimal amount, which is how the lips 34 prevent fluid from flowing upwardly through valve member 16, which could lead to contamination of the supply of fluid above the valve member 16.

One important aspect of the present invention is the manner in which the valve member 16 is seated within the valve seating section 26. Referring now to FIG. 1, the valve member 16 is shown seated within the lower housing 14, and with the upper housing 12 in place. The flange 30 should have an outer diameter which is slightly larger than the diameter of an axially extending inner peripheral surface 38 (also shown in FIG. 2) of the valve seating section 26. Thus, the flange 30 creates a press-fit type of arrangement with the inner peripheral surface 38 to retain the valve member 16 in place within the lower housing 14. Tests have shown that if the flange diameter is between approximately 0.005 and 0.021 inch larger than the valve seating section diameter, the valve member 16 will be securely seated within the lower housing 14, and will also be able to maintain a seal between these two components. After the valve member 16 is seated within the lower housing 14, the upper housing 12 and the lower housing 14 are connected together, preferably via sonic welding, to form a complete housing assembly.

The press-fit creates a radial compression that maintains the valve member 16 in place, and eliminates the need for the axial compression previously relied upon for the same purpose. In prior art devices that relied upon axial compression to maintain the valve member in place within the housing, the flange was compressed between the upper housing and the lower housing. Accordingly, the lower transverse surface of the flange was pressed against a counterpart transverse surface on the housing. Such a configuration made it difficult to weld the two housing components together because of the intervening flange. Moreover, unless care was taken to ensure that the valve member remained properly aligned during the welding, the valve member could become tilted within the housing, and the outer periphery of the lips could contact the inner periphery of the housing. Such contact between the valve member and the housing could result in failure of the valve member because the housing is interfering with the operation of the resilient lips, i.e., the resilient lips may not open/close the aperture at the appropriate times. In addition, obtaining welds of consistent strength is also difficult when the valve member is retained by axial compression.

In contrast, the present invention (which does not rely upon axial compression to seat the valve member 16 within the valve seating section 26 of the lower housing 14, but instead relies upon radial compression) eliminates the problems associated with axial compression. Securing the valve member 16 via radial compression essentially ensures that the valve member 16 is properly seated, centered and aligned within the valve seating section 26, which minimizes the chance that the outer periphery of the barrel portion 32 will contact the inner periphery of the housing. Thus, the resilient lips 34 will be able to open and close the slit 36 at the proper times because their operation will not be hindered by contact with the housing.

It should be noted that an air space 40 (FIG. 1) is defined between a lower transverse surface 42 of the flange 30 (see also FIGS. 4 and 5) and a transversely extending surface 44 of the valve seating section 26. The air space 40 prevents the flange 30 from being loaded under any axially compressive forces when the upper housing 12 and the lower housing 14 are mated. Thus, even if either the lower transverse surface 42 of the flange 30 or the transversely extending surface 44 of the valve seating section 26 contains a small protrusion or is not perfectly flat, the valve member 16 can still be properly seated within the valve seating section 26 because of the air space 40. A suggested axial length of the air space 40 is 0.010 inch.

Attention is drawn to the fact that in the preferred embodiment, the collar 28 on the valve member 16 has a larger diameter than that of the flange 30. Preferably, when the valve member 16 is seated within the lower housing 14, the upper surface 46 of the valve member 16 is coplanar with the upper surface 48 of the lower housing 14. To enable this coplanar or flush seating arrangement, a recess 29 for seating the collar 28 is provided in the lower housing 14, as shown in FIGS. 1 and 2.

While manufacturing and handling the valve members prior to placement of the valve members into the housing, the valve members sometimes have a tendency to adhere to the planar surfaces of the feeder bins that are used to feed the valve members from one processing area to the next. This adherence is exacerbated by the presence of oils or other lubricants on the planar surface. To resolve this difficulty, an upper ring 52 and a lower ring 54 may be added to the upper and lower surfaces, respectively, of the valve member 16, as best shown in FIGS. 4 and 5. Therefore, regardless of whether the valve member 16 is upright or inverted, one of the rings will serve to minimize the surface area contacting the planar surface of the bin, and reduce adhesion between the valve member and the bin.

While various embodiments of the present invention have been shown and described, it should be understood that other modifications, substitutions and alternatives may be apparent to one of ordinary skill in the art. Such modifications, substitutions and alternatives can be made without departing from the spirit and scope of the invention, which should be determined from the appended claims.

Various features of the invention are set forth in the appended claims.

What is claimed is:

1. A check valve assembly comprising:

a housing, wherein said housing defines a valve seating section within an inner peripheral portion thereof, said valve seating section including an axially extending inner peripheral first surface and a second surface extending generally transversely and generally radially inwardly from said first surface, said second surface extending from a lower end of said first surface;

a valve member including a main body portion extending in a generally axial direction;

a flange positioned on said main body portion, said flange extending in a direction generally transverse to said axial direction and including an outer periphery thereon, wherein said flange outer periphery is configured and arranged to be seated in said housing by being press-fit therein, whereby said flange outer periphery is compressed by said housing primarily in the transverse direction, wherein said valve member is retained within said housing primarily via said press-fit, and without relying upon any significant axial compression of said flange, and further wherein a space is defined between said second surface of said housing and a lower surface of said flange; and valve means for allowing fluid to pass through said valve member from a first direction and for preventing fluid from passing through said check valve in a second direction opposite to the first direction.

2. The check valve assembly as defined in claim 1 wherein said flange is configured and arranged to be seated in said housing such that an air space is defined axially below said flange, between said flange and said housing.

3. The check valve assembly as defined in claim 1 wherein said valve means comprises a pair of lips positioned radially within said main body portion, said pair of lips extending from an area near an upper region of said main body portion to an area near a lower region of said main body portion, said lips resiliently converging towards said lower region of said main body portion to terminate in a normally closed aperture that opens in response to a predetermined amount of pressure acting thereon, allowing fluid to pass through said valve member in the first direction upon opening of said normally closed aperture.

4. The check valve assembly as defined in claim 1 wherein said valve member is generally cylindrical and includes an upper surface and a lower surface, and wherein said valve member further comprises:

an upper ring positioned on and extending from the upper surface; and a lower ring positioned on and extending from the lower surface.

5. The check valve assembly defined in claim 1 wherein said flange is retained within said housing solely via said press-fit, without any reliance upon axial compression.

6. The check valve assembly as defined in claim 1 further comprising a collar located axially above said flange and including an outer periphery thereof that is greater in said transverse direction than said outer periphery of said flange.

7. The check valve assembly as defined in claim 6 wherein said collar includes a lower surface thereof, and further wherein said lower surface of said collar contacts a portion of said housing.

8. A valve assembly for permitting fluid flow in a first direction and for preventing fluid flow in a second direction opposite to the first direction, said valve assembly comprising:

an upper housing;

a lower housing coupled to said upper housing to form a generally axially extending housing assembly;

a valve seating section defined within an inner peripheral portion of said lower housing, said valve seating section including an axially extending inner peripheral surface and a transversely extending surface substantially normal to said axially extending inner peripheral surface;

a valve member seated within said valve seating section of said lower housing;

a flange positioned on said valve member, said flange extending from said valve member in a transverse direction and defining an axially oriented outer peripheral surface thereof; and wherein said valve member is retained within said valve seating section by said axially extending inner peripheral surface of said valve seating section transversely compressing said axially oriented outer peripheral surface of said flange in a press-fit arrangement, wherein said valve member is retained within said lower housing primarily via said press-fit, and without relying upon any significant axial compression of said flange, and further wherein a space is defined between said transversely extending surface of said valve seating section and said flange.

9. The valve assembly defined in claim 8 further comprising a lower transverse surface defined on said flange, wherein said lower transverse surface of said flange is axially separated from said transversely extending surface of said valve seating section whereby an air space is defined therebetween.

10. The valve assembly defined in claim 8 wherein said inner peripheral surface of said valve seating section and said axially oriented outer peripheral surface of said flange are both generally cylindrical and said inner peripheral surface of said valve seating section is of a diameter that is slightly less than that of said axially oriented outer peripheral surface of said flange whereby said press-fit is created therebetween.

11. The valve assembly defined in claim 8 wherein said valve member includes an upper surface thereof, and whereby said upper surface of said valve member is substantially parallel with an upper surface of said lower housing.

12. The valve assembly defined in claim 8 wherein said valve member is generally cylindrical and includes an upper surface and a lower surface, and wherein said valve member further comprises:
   an upper ring positioned on and extending from the upper surface; and
   a lower ring positioned on and extending from the lower surface.

13. The valve assembly defined in claim 8 wherein said valve member includes a barrel section which has a generally cylindrical outer peripheral surface, said lower housing includes a generally cylindrical inner peripheral surface opposed to said generally cylindrical outer surface of said barrel section of said valve member, and whereby said outer peripheral surface of said barrel section of said valve member is positioned in a spaced relationship from said inner peripheral surface of said lower housing.

14. The valve assembly defined in claim 8 wherein said valve member comprises a pair of lips positioned radially within a barrel section, said pair of lips extending from an area near an upper region of said barrel section to an area near a lower region of said barrel section, said lips resiliently converging towards said lower region of said barrel section and terminating in a normally closed aperture that opens in response to a predetermined amount of pressure acting thereon, thereby allowing fluid to pass through the valve member in the first direction.

15. The valve assembly defined in claim 8 wherein said flange is retained within said valve seating section solely via said press-fit, without any reliance upon axial compression originating from said lower housing.

16. The valve assembly as defined in claim 8 further comprising a collar located axially above said flange and including an outer periphery thereof that extends farther in said transverse direction than said axially oriented outer peripheral surface of said flange.

17. The valve assembly as defined in claim 16 wherein said collar includes a lower surface thereof that extends generally parallel to said transverse direction, and further wherein said lower surface of said collar contacts a generally transversely extending collar seating portion of said lower housing.

18. A duckbill valve assembly for permitting fluid flow in a first direction and for preventing fluid flow in a second direction opposite to the first direction, said duckbill valve comprising:
   an upper housing member;
   a lower housing member coupled to said upper housing member to form a generally axially extending housing assembly, said lower housing member defining a valve seating section within an inner peripheral portion of said lower housing member, said valve seating section including an axially extending inner peripheral first surface and a second surface extending generally transversely and generally radially inwardly from said first axially extending surface, said second surface extending from a lower end of said first surface;
   a valve member positioned within said housing assembly, said valve member including a barrel portion extending generally in an axial direction from an upper region to a lower region thereof;
   a flange located near said upper region of said barrel portion, said flange defining an outer flange periphery that is configured and arranged to be seated, in a press-fit arrangement, within an inner periphery of said valve seating section of said lower housing member via radial compression of said flange by said inner periphery of said valve seating section of the housing member, wherein said valve member is retained within said lower housing primarily via said press-fit, and without relying upon any significant axial compression of said flange, and further wherein a space is defined between said second surface of said lower housing member and said flange of said valve member; and
   a pair of lips positioned radially within said barrel portion and extending from an area near said upper region of said barrel portion to an area near said lower region of said barrel portion, said lips resiliently converging towards said lower region of said barrel portion to terminate in a normally closed aperture that opens in response to a predetermined amount of pressure acting within said barrel portion, thereby allowing fluid to pass through said valve member in the first direction.

19. The duckbill valve assembly defined in claim 18 wherein said flange includes a lower surface thereof which is configured and arranged to be axially separated from a transversely extending surface of said valve seating section such that an air space is defined therebetween.

20. The duckbill valve assembly defined in claim 18 wherein said valve member is configured and arranged such that when said valve member is seated within said housing, an outer peripheral surface of said barrel portion is separated from an inner peripheral surface of said housing.

21. The duckbill valve assembly defined in claim 18 wherein an outer peripheral surface of said barrel portion is generally cylindrical.

22. The duckbill valve assembly defined in claim 18 wherein said valve member is generally cylindrical and includes an upper surface and a lower surface, and wherein said valve member further comprises:

an upper ring positioned on and extending from the upper surface; and a lower ring positioned on and extending from the lower surface.

23. The duckbill valve assembly defined in claim 18 wherein said flange is retained within said valve seating section solely via said press-fit, without any reliance upon axial compression originating from said lower housing.

24. The duckbill valve assembly as defined in claim 18 further comprising a collar located axially above said flange and including an outer periphery thereof that is greater in said transverse direction than said outer periphery of said flange.

25. The duckbill valve assembly as defined in claim 24 wherein said collar includes a lower surface thereof that extends generally parallel to said transverse direction, and further wherein said lower surface of said collar contacts a generally transversely extending collar seating portion of said lower housing.

26. A valve assembly for permitting fluid flow in a downstream direction and for preventing fluid flow in an upstream direction generally opposite to the downstream direction, said valve assembly comprising:

an upper housing;

a lower housing coupled to said upper housing to form a generally axially extending housing assembly, said lower housing defining a valve seating section within an inner peripheral portion of said lower housing, said valve seating section including an axially extending inner peripheral first surface and a second surface extending transversely and radially inward from said first axially extending surface, said second surface extending from a lower end of said first surface;

a valve member positioned within said housing assembly, said valve member including a lower portion extending generally in an axial direction from an upper region to a lower region, said lower portion being configured such that said lower portion is generally spaced from said housing when said valve member is centered relative to said housing, said lower portion including a pair of lips extending from said upper region to said lower region, said lips configured to allow flow in said downstream direction upon the application of a predetermined amount of pressure and prevent flow in said upstream direction, said valve member further including a generally radially extending upper surface and a flange extending outward from said upper region of said lower portion, said flange defining an outer generally annular periphery and a lower surface extending generally radially inward from said periphery, said second surface of said housing extending generally toward said upper end of said lower region of said flange;

said first surface of said lower housing configured to contact said periphery of said flange and transversely compress said flange sufficiently enough to, prior to assembly of said upper housing to said lower housing, position said flange against movement relative to said lower valve housing with said lower portion centered relative to said lower valve housing and position said flange to define a space between said second surface of said lower housing and said lower surface of said valve.

27. The valve assembly of claim 26 wherein said valve includes a collar upstream of said flange and having an outer periphery outward of said outer periphery of said flange, said housing defines a recess, said collar disposed within said recess.

28. The valve assembly of claim 26 wherein the axial length of said space is about 0.010 inches.

29. The valve assembly of claim 26 wherein said lower housing and said upper housing are configured to not apply axial compression to said flange when said lower housing and upper housing are connected to form said housing assembly.

* * * * *